US011279671B2

(12) United States Patent
Bertini et al.

(10) Patent No.: US 11,279,671 B2
(45) Date of Patent: Mar. 22, 2022

(54) PROCESS AND PLANT FOR THE SYNTHESIS OF UREA

(71) Applicant: Casale SA, Lugano (CH)

(72) Inventors: Paolo Bertini, Lugano (CH); Matteo Fumagalli, San Fermo della Battaglia (IT); Serena Gabbiadini, Milan (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/611,037

(22) PCT Filed: Apr. 30, 2018

(86) PCT No.: PCT/EP2018/061025
§ 371 (c)(1),
(2) Date: Nov. 5, 2019

(87) PCT Pub. No.: WO2018/202619
PCT Pub. Date: Nov. 8, 2018

(65) Prior Publication Data
US 2020/0190023 A1    Jun. 18, 2020

(30) Foreign Application Priority Data

May 5, 2017 (EP) .................................... 17169655

(51) Int. Cl.
*C07C 273/04* (2006.01)
*C07C 273/16* (2006.01)

(52) U.S. Cl.
CPC .......... *C07C 273/04* (2013.01); *C07C 273/16* (2013.01)

(58) Field of Classification Search
CPC ................ C07C 273/04; C07C 273/16; C07C 273/1836
See application file for complete search history.

(56) References Cited

U.S. PATENT DOCUMENTS

| | | | | |
|---|---|---|---|---|
| 2,913,493 A * | 11/1959 | Sze | ....................... | C07C 273/04 564/72 |
| 3,091,637 A * | 5/1963 | Cook | .................... | C07C 273/04 564/72 |
| 3,317,601 A * | 5/1967 | Otsuka | .................. | C07C 273/04 564/67 |
| 3,354,205 A * | 11/1967 | Marten | ................. | C07C 273/04 564/71 |
| 3,470,247 A * | 9/1969 | Guadalupi | ............ | C07C 273/04 564/72 |
| 3,579,636 A * | 5/1971 | Marovic | ............... | C07C 273/04 564/71 |
| 3,607,938 A * | 9/1971 | Braun | .................. | C07C 273/04 564/70 |
| 3,636,106 A * | 1/1972 | Villiers-Fisher | ...... | C07C 273/04 564/71 |
| 3,759,992 A * | 9/1973 | Mavrovic | ............. | C07C 273/04 564/67 |
| 3,808,271 A * | 4/1974 | Marovic | ............... | C07C 273/04 564/72 |
| 3,824,283 A * | 7/1974 | Harada | .................. | C07C 273/04 564/71 |
| 3,886,210 A | 5/1975 | Mavrovic | | |
| 3,932,504 A * | 1/1976 | Chen | ......................... | B01J 3/04 564/71 |
| 4,296,252 A | 10/1981 | Mavrovic | | |
| 4,540,813 A | 9/1985 | van Nassau et al. | | |
| 4,864,059 A | 9/1989 | Fujii | | |
| 5,681,537 A * | 10/1997 | Pagani | .................. | C07C 273/04 203/31 |
| 7,608,735 B2 * | 10/2009 | Zardi | .................... | C07C 273/04 564/70 |
| 7,982,068 B2 * | 7/2011 | Zardi | .................... | C07C 273/04 564/67 |
| 8,927,770 B2 * | 1/2015 | Carlessi | ................ | C07C 213/04 564/71 |
| 10,550,075 B2 * | 2/2020 | Rugnone | ............... | C07C 273/16 |
| 2010/0063321 A1 * | 3/2010 | Zardi | .................... | C07C 273/04 564/71 |
| 2010/0069631 A1 * | 3/2010 | Zardi | .................... | C07C 273/12 544/222 |
| 2011/0110826 A1 * | 5/2011 | Mennen | ................ | C07C 273/04 422/187 |
| 2011/0124495 A1 * | 5/2011 | Zardi | .................... | C07C 273/16 502/167 |
| 2011/0160486 A1 * | 6/2011 | Gevers | .................. | C07C 273/04 564/67 |
| 2013/0079546 A1 * | 3/2013 | Takamatsu | ............... | B01J 12/00 560/157 |

(Continued)

FOREIGN PATENT DOCUMENTS

WO    2013/165246 A1    11/2013

OTHER PUBLICATIONS

H. Irazoqui et al., 32 Ind. Eng. Chem. Res., 2671-2680 (1993) (Year: 1993).*

(Continued)

*Primary Examiner* — Alexander R Pagano
(74) *Attorney, Agent, or Firm* — Akerman LLP

(57) ABSTRACT

Plant for the synthesis of urea comprising: a synthesis section (101), wherein ammonia (1) and carbon dioxide (2) react to give an aqueous solution (3) containing urea and ammonium carbamate; at least one recovery section fed with said depressurized aqueous solution and in a two-phase state, said recovery section comprising a separator (104,108) which processes said two-phase solution; a pre-decomposer (105, 109), a decomposer (106, 110) and a condenser (107, 111), wherein the gaseous streams obtained in the separator and in the decomposer are condensed in said condenser of the recovery section.

1 Claim, 2 Drawing Sheets

(56) References Cited

U.S. PATENT DOCUMENTS

| | | | | |
|---|---|---|---|---|
| 2014/0081046 A1* | 3/2014 | Carlessi | ............... | C07C 273/04 564/71 |
| 2014/0330040 A1* | 11/2014 | Sioli | ................ | C07C 273/04 564/72 |
| 2015/0133690 A1* | 5/2015 | Mennen | ................ | B01D 5/006 564/67 |
| 2015/0322000 A1* | 11/2015 | Buitink | ................ | B01J 19/02 564/66 |
| 2015/0343409 A1* | 12/2015 | Buitink | ................ | C07C 273/04 29/401.1 |
| 2016/0288077 A1* | 10/2016 | Scotto | ................ | B01J 10/00 |
| 2016/0318855 A1* | 11/2016 | Meißner et al. | ........ | C01B 3/025 |
| 2017/0204054 A1* | 7/2017 | Mennen | ............... | B01D 21/262 |
| 2017/0327461 A1* | 11/2017 | Singh | ................ | C07C 273/16 |
| 2018/0208551 A1* | 7/2018 | Estefano Lagarrigue | ................ | C07C 273/04 |
| 2018/0258033 A1* | 9/2018 | Baharuddin | ........... | C07C 273/04 |
| 2018/0258034 A1* | 9/2018 | Sato | ................ | C07C 273/16 |
| 2018/0362452 A1* | 12/2018 | Rugnone | ............... | B01D 1/065 |
| 2019/0276325 A1* | 9/2019 | Bruno | ................ | C07C 273/04 |
| 2019/0359558 A1* | 11/2019 | Rugnone | ................ | C05C 9/005 |
| 2020/0002273 A1* | 1/2020 | Nettuno | ................ | C01B 3/025 |
| 2020/0385339 A1* | 12/2020 | Patil | ................ | B01J 3/04 |

OTHER PUBLICATIONS

Reasoned Statement of Opposition in Opposition against European Patent No. 3619194 (Dec. 3, 2021) (Year: 2021).*
International Search Report issued in connection with PCT/EP2018/061025.
International Preliminary Report on Patentability issued in connection with PCT/EP2018/061025.
Notice of Opposition filed by Stamicarbon B.V. in connection with EP3619194B1.
Meessen, Jozef H., "Urea", Ullmann's Encyclopedia of Industrial Chemistry, 2010, Wiley-VCH Verlag GmbH & Co., pp. 1-39.
Meessen, Jozef H., "Urea", Ullmann's Encyclopedia of Industrial Chemistry, 1996, Wiley-VCH Verlag GmbH & Co., vol. A27, pp. 333-365.
Programme Ninth Stamicarbon Urea Symposium Renaissance Amsterdam Hotel, May 8-May 11, 2000.
Jonckers, K., "New Developments in Stamicarbon's Urea 2000 Plus Process," Fertiliser Industry, 2000, pp. 57-63.
New Developments in Stamicarbon's Urea 2000 Plus Process, Paper 8.
Jonckers, K., "New Developments in Stamicarbon's Urea 2000 Plus Process," 9th Stamicarbon Urea Symposium, May 8-11, 2000, Amsterdam.

* cited by examiner

PROCESS AND PLANT FOR THE SYNTHESIS OF UREA

CROSS-REFERENCE TO RELATED APPLICATIONS

This application is a national phase of PCT/EP2018/061025, filed Apr. 30, 2018, and claims priority to EP 17169655.2, filed May 5, 2017, the entire contents of both of which are hereby incorporated by reference.

FIELD OF APPLICATION

The invention relates to a process and plant for the synthesis of urea. The invention also relates to a method for revamping an existing plant for the synthesis of urea.

PRIOR ART

Plants for the synthesis of urea from ammonia and carbon dioxide generally comprise a high-pressure synthesis section and at least one low-pressure recovery section. Such plants are described in the literature, for example in Meessen, "Urea", Ullmann's Encyclopedia of Industrial Chemistry, Wiley-VCH Verlag, 2010.

The high-pressure synthesis section typically comprises at least a reactor, a stripper and a condenser, which form a synthesis loop and operate substantially at the same pressure of about 120-180 bar.

Ammonia and carbon dioxide react in the aforementioned reactor to produce an aqueous solution essentially containing urea, unconverted ammonium carbamate and free ammonia. This solution is sent to the stripper where the unconverted carbamate is decomposed into ammonia and carbon dioxide.

A urea more concentrated aqueous solution and a gas flow containing ammonia and carbon dioxide are obtained at the output of the stripper. The aqueous solution is sent to said recovery section, while the gas are at least partially condensed in the condenser and the condensate so obtained is recycled back to the reactor.

Some plants of the prior art comprise a medium-pressure recovery section and a low-pressure recovery section arranged in series. Said recovery sections each comprise a section for the decomposition of the unreacted carbamate and a condenser, and operate respectively at a pressure of about 12-30 bar and 2-10 bar.

An aqueous solution of urea with a concentration of about 65-75% is obtained at the output of the low-pressure section. For example, said solution is sent to an evaporation section, where it is concentrated to give a urea melt, and the urea melt is for example fed to a finishing (shaping) section so as to provide solid urea in the form of granules or prills.

The content of water in the urea aqueous solution obtained at the outlet of the synthesis section is determined by the water produced in the urea synthesis reaction and the water supplied by recycling the condensate back to the reactor.

A significant amount of water contained in said urea aqueous solution is separated from urea in the carbamate decomposition sections, and another amount in the evaporation section. The former amount is recycled back to the synthesis section, resulting in a decreased conversion to urea, in a greater amount of ammonium carbamate in the effluent of the reactor and therefore in a greater steam consumption for the carbamate dissociation. The latter amount, on the other hand, is subjected to a waste water treatment and the treated water is mainly purged, while only a controlled minor amount thereof is recycled back to the condenser of a low-pressure recovery section to ensure the condensation of ammonia and carbon dioxide.

Furthermore, especially during revamping operations which involve a capacity increase of the synthesis section, the medium-pressure and low-pressure recovery sections become a bottle neck of the plant. In this situation, these recovery sections receive a greater flowrate of urea solution, and therefore a significantly higher quantity of carbamate to be decomposed. Since the apparatuses of the recovery sections (decomposers, condensers, etc.) are generally close to their maximum capacity, these sections are unable to cope with the increased capacity of the synthesis section.

The installation of larger apparatuses would result in very high costs and therefore is not very attractive. There is an incentive to attempt to increase the capacity of the urea plants while reducing the modifications to the recovery sections, in order to reduce costs. To this purpose, in the prior art it has also been proposed to insert a pre-decomposer upstream of the decomposer. Not even this solution, however, is entirely satisfactory because said pre-decomposer is subject to a high load and consequently is a costly apparatus. Moreover the installation of a pre-decomposer does not substantially reduce the quantity of water recycled to the synthesis section, which, as known, is undesirable.

SUMMARY OF THE INVENTION

The invention proposes to improve the technology and to reduce the investment costs for increasing the capacity of urea plants. In particular, the invention proposes to improve the technology for increasing the capacity of the recovery section(s) of a urea plant provided with pre-decomposer. It is also desirable to minimize the amount of water separated in the decomposition section.

These objects are achieved with a plant for the synthesis of urea from ammonia and carbon dioxide which comprises:
a synthesis section, in which ammonia and carbon dioxide react producing urea at a synthesis pressure;
at least one recovery section operating at a recovery pressure lower than said synthesis pressure;
a line which supplies an aqueous solution containing urea to said at least one recovery section, said line comprising at least one intercepting member suitable for depressurizing the aqueous solution with formation of a two-phase flow;
wherein said at least one recovery section comprises:
a separator which receives said two-phase flow and separates the gaseous phase from the liquid phase, producing a first gaseous stream containing ammonia and carbon dioxide, and a liquid stream containing water, urea and ammonium carbamate;
a pre-decomposer which receives said liquid stream from the separator and wherein at least a part of the ammonium carbamate is decomposed, obtaining an effluent containing residual ammonium carbamate;
a decomposer which receives the effluent of said pre-decomposer and wherein at least a part of the residual ammonium carbamate is decomposed to give a second gaseous stream containing ammonia and carbon dioxide and an aqueous solution containing urea,
a condenser, wherein said first gaseous stream and said second gaseous stream are at least partially condensed.
The aforementioned intercepting member is preferably a valve.

Inside the synthesis section the ammonia and the carbon dioxide react to give an aqueous solution containing urea and ammonium carbamate.

Said line which supplies an aqueous solution containing urea to said at least one recovery section may, in some embodiments, be a line coming from the synthesis section, for example supplying the effluent of a synthesis reactor or of a stripper. In other embodiments said line comes from a recovery section operating at higher pressure. For example said line may supply an aqueous solution containing urea from the decomposer of a first recovery section to the separator of a following recovery section.

The effluent of the pre-decomposer is preferably in a two-phase state and comprises water, urea and residual ammonium carbamate in the liquid phase and ammonia and carbon dioxide in the gaseous phase.

A solution of ammonium carbamate is obtained in the condenser, which is advantageously recycled back to the synthesis section.

The synthesis section comprises, in some embodiments, a plurality of apparatuses which operate essentially at the same pressure, forming a synthesis loop. Preferably, said synthesis loop comprises a reactor, a stripper and a condenser.

The synthesis pressure is operated preferably at 120-180 bar.

In the stripper of the synthesis loop, if provided, the ammonium carbamate is dissociated by means of heat addition, for example by means of steam. In an embodiment of the invention, the synthesis loop comprises a stripper which is also fed with a flow of carbon dioxide acting as stripping agent (CO2 stripping). In other embodiments stripping is performed without the addition of CO2 (so-called self-stripping or thermal stripping). The invention is also applicable to plants whose synthesis section does not comprise a stripper.

According to an embodiment of the invention, the plant comprises a plurality of recovery sections arranged in series and operating at decreasing pressures. A first recovery section receives the aqueous solution leaving the synthesis section, for example leaving a stripper of a synthesis loop; each recovery section following the first one processes the aqueous solution leaving the preceding section at a lower pressure.

In a first embodiment, said first recovery section comprises the aforementioned separator, pre-decomposer, decomposer and condenser. As a consequence, the plant comprises a line which supplies the aqueous solution coming from the synthesis to the separator of said first recovery section.

In a second embodiment, each of said recovery sections comprises, respectively, a separator, a pre-decomposer, a decomposer and a condenser. In this embodiment, the plant advantageously comprises a first line which supplies said aqueous solution from the synthesis section to the first recovery section, and further lines which supply aqueous solutions from the decomposer of one recovery section to the separator of the following recovery section.

According to a preferred embodiment, said plant comprises two recovery sections in series, i.e. a medium-pressure section and a low-pressure section, respectively. Preferably, the medium-pressure section operates at about 12-30 bar and the low-pressure section operates at about 2-10 bar. In some embodiments a recovery section operating at a medium-high pressure from 50 to 80 bar is provided. Said medium-high pressure recovery section is preferably in combination with a medium-pressure section and/or a low-pressure section.

Preferably, the separator and the pre-decomposer of said at least one recovery section are separate apparatuses, i.e. they are housed into respective pressure shells. In some embodiments said separator and pre-decomposer may also be advantageously combined in a single apparatus. The separator combined with the pre-decomposer is advantageously situated above (at the top of) the pre-decomposer. The combined separator and pre-decomposer may be housed inside the same shell.

Preferably, said pre-decomposer is a tube-bundle exchanger which uses steam as heat-exchange fluid.

Further aspects of the invention relate to a process for the synthesis of urea from ammonia and carbon dioxide and a revamping method according to the accompanying claims.

The invention offers several advantages compared to the prior art.

Firstly, the presence of a separator upstream of the pre-decomposer reduces the material and thermal load of the pre-decomposer. Consequently, the pre-decomposer may be designed with smaller dimensions compared to the plants of the prior art.

Another advantage is given by a lower material and thermal load of the condenser of the recovery section.

The presence of the separator also results in a more appropriate separation of the water. The gaseous phase containing ammonia and carbon dioxide directed to the condenser and the ammonium carbamate solution leaving the condenser itself contain less water with respect to the prior art.

This smaller content of water results in a lower consumption of the pumps recycling the carbamate solution to the synthesis section. Moreover, the conversion to urea is increased thanks to the smaller amount of water recycled to the synthesis section. A smaller amount of water in the synthesis section results in a smaller amount of ammonium carbamate in the effluent of the reactor and therefore in a smaller steam consumption for the carbamate dissociation and the recovery of the reagents, in the recovery sections and, if present, in the stripper of the synthesis loop.

The detailed description which follows relates to preferred embodiments, which are described by way of a non-limiting example.

DETAILED DESCRIPTION

Figure 1:
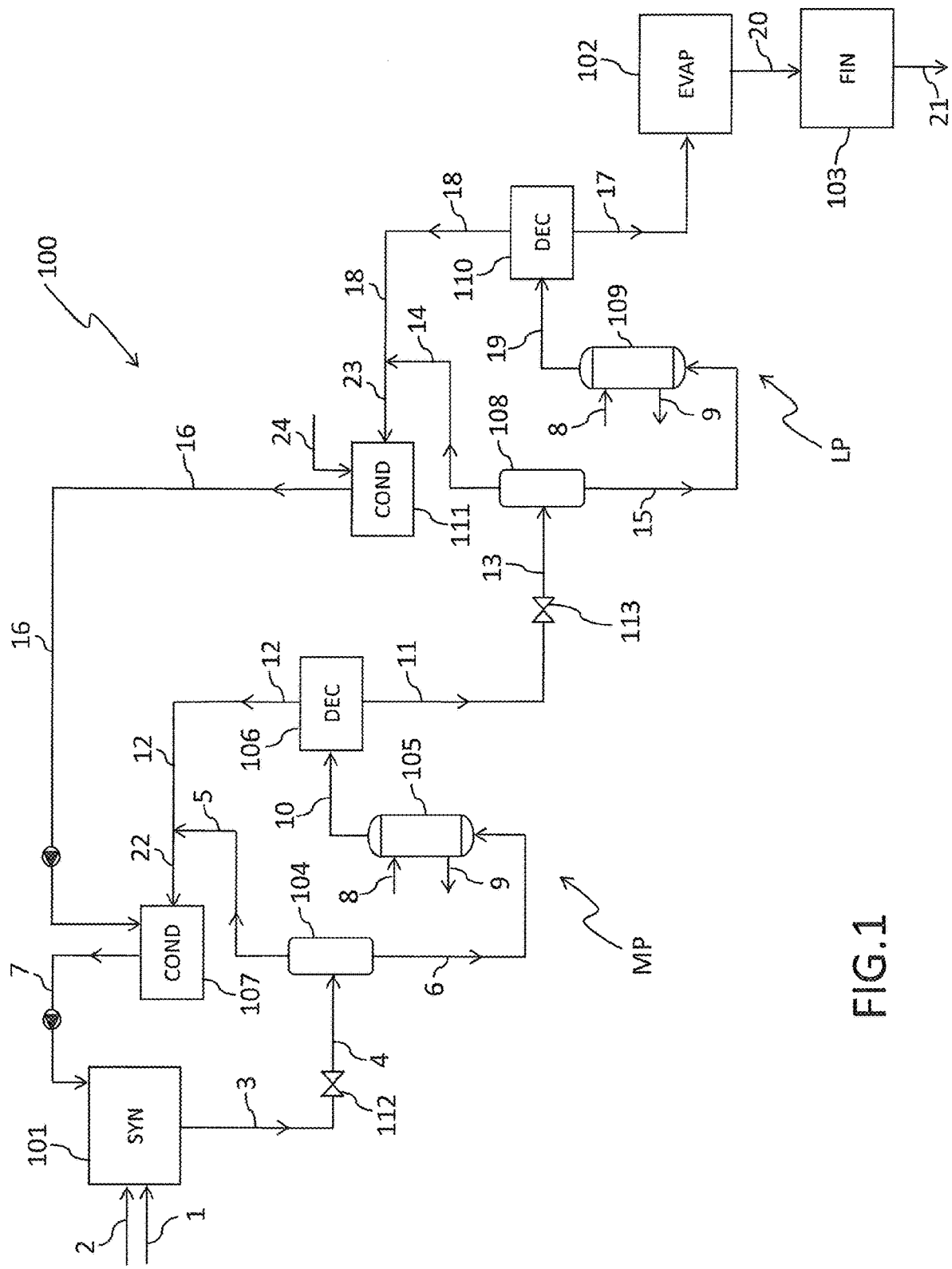
FIG. 1 shows a block diagram of a plant for the synthesis of urea according to a preferred embodiment of the invention.

FIG. 1 shows in schematic form a plant 100 for the synthesis of urea starting from ammonia and carbon dioxide. This plant 100 essentially comprises a high-pressure synthesis loop 101, a medium-pressure recovery section MP, a low-pressure recovery section LP, an evaporation section 102 and a finishing section 103.

The synthesis loop 101 operates at a pressure of about 120-180 bar; the recovery section MP operates at a pressure of about 12-30 bar and the recovery section LP operates at a pressure of about 2-10 bar.

The synthesis loop 101 comprises a reactor, a stripper, a scrubber and a condenser (not shown). The recovery section MP comprises a separator 104, a pre-decomposer 105, a decomposer 106 and a condenser 107. Similarly, the recovery section LP comprises a separator 108, a pre-decomposer 109, a decomposer 110 and a condenser 111.

The plant 100 essentially operates as follows.

Ammonia 1 and carbon dioxide 2 are fed to the synthesis loop 101, where they react to give an aqueous solution 3 essentially comprising urea and unconverted ammonium carbamate.

The solution 3 coming from the synthesis loop 101 is depressurized in a valve 112. The solution 4 leaving said valve 112 is in a two-phase liquid/gas state and comprises water, urea and carbamate in the liquid phase and ammonia and carbon dioxide in the gaseous phase. Said solution 4 is sent to the separator 104 of the section MP, which separates the gaseous phase at the top and the liquid phase at the bottom, obtaining a first gaseous stream 5 and a liquid stream 6.

Said first gaseous stream 5 is mixed with a second gaseous stream 12 leaving the decomposer 106, thus forming a stream 22. Said stream 22 is than sent to the condenser 107 of the section MP, where it is condensed to give a solution 7 containing ammonium carbamate. Said solution 7 is recycled back to the synthesis loop 101. In a variant, the gaseous streams 5 and 12 are sent separately to the condenser 107.

The liquid stream 6 is sent to the pre-decomposer 105 of the section MP, where the ammonium carbamate contained therein is partially decomposed. Said pre-decomposer 105 is preferably a tube bundle heat exchanger wherein the liquid phase 6 is introduced on the tube side and the steam 8 is introduced on the shell side, providing condensed steam 9.

Figure 2:
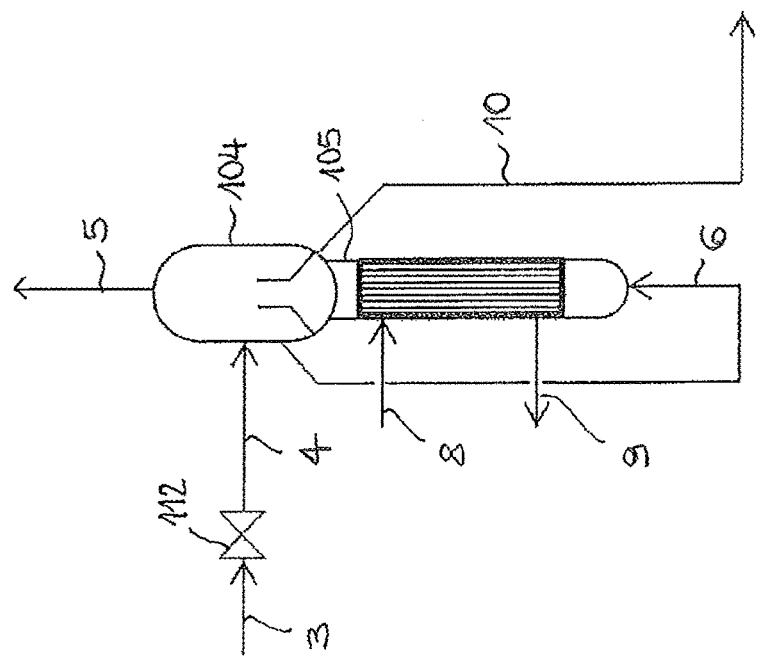
FIG. 2 shows a first layout in which separator and pre-decomposer are two separate apparatuses.
Figure 3:
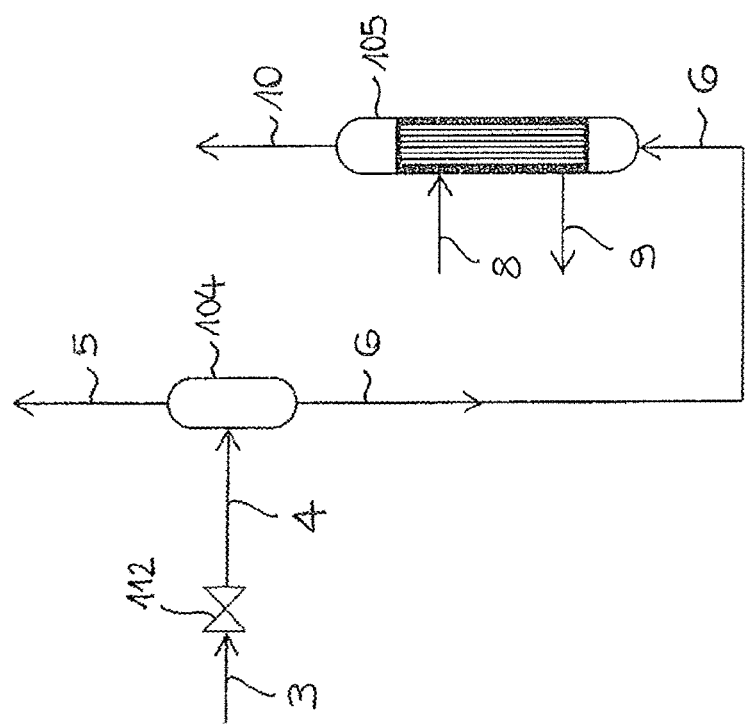
FIG. 3 shows a second layout in which separator and pre-decomposer are combined in a single apparatus.

The separator 104 and the pre-decomposer 105 may be two separate apparatuses (FIG. 2) or may be combined in a single apparatus (FIG. 3).

The effluent 10 of the pre-decomposer is fed to the decomposer 106, where the ammonium carbamate is further decomposed. At the output of the decomposer 106 the following are obtained: an aqueous solution 11 containing urea and residual ammonium carbamate, which is further processed in the recovery section LP, and a second gaseous stream 12 containing ammonia and carbon dioxide, which is sent to the condenser 107 as stream 22 so as to produce the aforementioned solution 7 containing ammonium carbamate.

The aqueous solution 11 is depressurized in a valve 113 and the solution 13 leaving the valve 113 is in a two-phase state comprising water, urea and carbamate in the liquid phase, and ammonia and carbon dioxide in the gaseous phase. Said solution 13 is sent to the separator 108 of the section LP, which separates the gaseous phase 14 at the top and the liquid phase 15 at the bottom.

The gaseous phase 14 is mixed with the gaseous stream 18 leaving the decomposer 110 to provide a stream 23 directed to the condenser 111 of the section LP. Said condenser 111 is also fed with an aqueous stream 24 coming from a water treatment section of the plant (not shown). At the output of the condenser 111, a condensate 16 is obtained, which is preferably sent to the condenser 107 of the section MP, in order to promote the condensation of the gaseous stream 22. In a variant, the gaseous streams 14 and 18 are fed separately to the condenser 111.

The liquid phase 15 is sent to the pre-decomposer 109 of the section LP. The effluent 19 of the pre-decomposer 109 is fed to the decomposer 110, obtaining an aqueous solution of urea 17 having a concentration of about 65-75%. At the output of said decomposer 110 a gaseous phase 18 is also obtained, which is in turn sent to the condenser 111.

Similarly to the separator 104 and the pre-decomposer 105 of the section MP, the separator 108 and the pre-decomposer 109 of the section LP may also be two separate apparatuses or combined in a single apparatus.

The urea solution 17 is then sent to the evaporation section 102, where it is concentrated to give urea melt 20. Said urea melt 20 is then fed to the granulation or prilling section 103 so as to produce solid urea 21 in the form of granules and/or prills.

Experimental Data

An aqueous solution leaves the synthesis section 101 at 204° C. and 143 barg. Said solution has the following composition:
free ammonia+equivalent ammonia: 24,322 kg;
equivalent CO2: 6,395 kg;
water: 24,516 kg;
urea: 41,667 kg.

The terms "equivalent ammonia" denotes the ammonia converted into ammonium carbamate and the terms "equivalent CO2" denotes the CO2 converted into ammonium carbamate.

Comparative Example (Before Revamping)

Reference is made to a plant comprising in series a MP recovery section and a LP decomposer. The MP section comprises a MP pre-decomposer and a MP decomposer.

|  | MP pre-decomposer | MP decomposer |
| --- | --- | --- |
| $P_{out}$ (barg) | 17.2 | 17.2 |
| $T_{out}$ (° C.) | 152 | 159 |
| Q (Gcal/h) | 3.91 | 1.81 |

|  | Gaseous stream from MP decomposer | Gaseous stream from LP decomposer |
| --- | --- | --- |
| Ammonia | 21'501 kg | 3'380 |
| CO2 | 5'460 kg | 867 kg |
| Water | 4'208 kg | 1'490 kg |
| Inerts | 436 kg | — |
| T (° C.) | 152 | 127 |
| P (barg) | 17.2 | 3.5 |

Example of the Invention (after Revamping)

Reference is made to a plant comprising in series a MP recovery section and a LP decomposer. The MP section comprises a separator, a MP pre-decomposer and a MP decomposer.

|  | MP pre-decomposer | MP decomposer | LP decomposer |
| --- | --- | --- | --- |
| $P_{out}$ (barg) | 17.2 | 17.2 | 3.5 |
| $T_{out}$ (° C.) | 153 | 159 | 143 |
| Q (Gcal/h) | 3.34 | 1.81 | 1.66 |

|  | Gaseous phase from separator | Gaseous stream from MP decomposer | Gaseous stream from LP decomposer |
|---|---|---|---|
| Ammonia | 14'231 kg | 7'211 kg | 3'475 kg |
| CO2 | 2'177 kg | 3'188 kg | 899 kg |
| Water | 1'819 kg | 1'603 kg | 1556 kg |
| inerts | — | 436 kg | — |
| T (° C.) | 141 | 152 | 127 |
| P (barg) | 17.5 | 17.2 | 3.5 |

It follows that:

|  | Gaseous stream from MP section | | Gaseous streams from MP section + LP decomposer | |
|---|---|---|---|---|
|  | Before revamp. | After revamp. | Before revamp. | After revamp. |
| Ammonia | 2'1501 kg | 2'1442 kg | 24'881 kg | 24'917 kg |
| CO2 | 5'460 kg | 5'365 kg | 6'327 kg | 6'264 kg |
| Water | 4'208 kg | 3'423 kg | 5'698 kg | 4'979 kg |
| T | 152° C. | 145° C. | | |

In the revamped plant, the gaseous streams from the MP section and LP decomposer account for an overall reduction of water of 719 kg, which is a significant amount.

This is thanks to the installation of the separator in the MP recovery section, which separates the gaseous phase before providing heat in the MP decomposer. As a result, the gaseous phase from the MP section is cooler (145° C.) and therefore has a lower content of water, which is the least volatile component.

The advantages of the revamped plant according to the present invention are summarized below.

First of all, the amount of water recycled to the synthesis is 719 kg less than the non-revamped plant. In particular: the ratio water/CO2 at the inlet of the synthesis reactor is reduced of about 7%; the CO2 conversion is increased of about 0.5%, and the HP steam consumption is reduced of about 4% (23 kg/MT);

Furthermore, the thermal load to the pre-decomposer is reduced of 15% and the thermal load to the MP condenser is reduced of 10%.

What is claimed is:

1. A method for revamping an existing plant for the synthesis of urea from ammonia and carbon dioxide, wherein the plant comprises:

a synthesis section, in which ammonia and carbon dioxide react at a synthesis pressure;

at least one recovery section which operates at a recovery pressure lower than said synthesis pressure and which is fed with a two-phase solution containing urea;

wherein said at least one recovery section comprises a pre-decomposer, a decomposer and a condenser;

said method comprising the installation in said at least one recovery section of a separator upstream of said pre-decomposer of the recovery section, said separator being fed with the two-phase solution;

said separator producing a liquid stream directed to the pre-decomposer further downstream, and a gaseous stream directed to said condenser of the recovery section;

wherein said separator, pre-decomposer, decomposer and condenser are arranged to operate at said recovery pressure lower than said synthesis pressure.

* * * * *